United States Patent [19]

Ritter et al.

[11] Patent Number: 5,854,007
[45] Date of Patent: Dec. 29, 1998

[54] PROCESS FOR PRODUCING GM1 SPECIFIC ANTIBODIES

[75] Inventors: Gerd Ritter; Lloyd J. Old, both of New York, N.Y.

[73] Assignee: Ludwig Institute For Cancer Research, New York, N.Y.

[21] Appl. No.: 847,369

[22] Filed: Apr. 24, 1997

Related U.S. Application Data

[62] Division of Ser. No. 491,310, Jun. 16, 1995, abandoned.

[51] Int. Cl.[6] .......................... G01N 33/574; G01N 33/53
[52] U.S. Cl. ..................... 435/7.23; 436/547; 530/387.7; 530/388.4; 530/388.8; 530/389.5
[58] Field of Search ........................... 435/7.23; 436/547; 530/387.7, 388.4, 388.8, 389.5

[56] References Cited

U.S. PATENT DOCUMENTS 4,957,741  9/1990  Kamarei et al. ..................... 424/551

OTHER PUBLICATIONS

Yuki, et al., *J. Exp. Med.*, vol. 178, pp. 1771–1775, Nov. 1993.

*Primary Examiner*—Toni R. Scheiner
*Attorney, Agent, or Firm*—Felfe & Lynch

[57] ABSTRACT

The invention relates to the production of ganglioside specific antibodies. These antibodies are produced following immunization with lipopolysaccharide antigen of *Campylobacter jejuni*. The antibodies bind to monosialogangliosides, including GM2 and GM1.

11 Claims, 4 Drawing Sheets

PROCESS FOR PRODUCING GM1 SPECIFIC ANTIBODIES

This application is a divisional of Ser. No. 08/491,310 filed Jun. 16, 1995, now abandoned.

FIELD OF THE INVENTION

This invention relates to the making of antibodies against glycolipids, and the uses of these antibodies. More particularly, it relates to processes for making antibodies specific to the monosialogangliosides known as "GM2" and "GM1", as well as the uses of these antibodies. The uses include diagnostic and screening applications, as well as therapeutic modalities.

BACKGROUND AND PRIOR ART

Gangliosides are a class of molecules which are glycolipids. Different gangliosides have been identified as prominent cell surface constituents of various transformed cells, including melanoma, as well as other tumors of neuroectodermal origin. See, e.g., Ritter and Livingston, et al., Sem. Canc. Biol. 2: 401–409 (1991). Oettgen, VCH Verlags Gesellschaft (Weinheim Germany 1989), incorporated by reference in their entirety.

Gangliosides are known as mono-, di-, tri or polysialogangliosides, depending upon the degree of glycosylation with sialic acid residues. Abbreviations employed to identify these molecules include "GM1", "GD3", "GT1", etc., with the "G" standing for ganglioside, "M", "D" or "T", etc. referring to the number of sialic acid residues, and the number or number plus letter (e.g., "GT1a"), referring to the binding pattern observed for the molecule. See Lehninger, Biochemistry, pg. 294–296 (Worth Publishers, 1981); Wiegandt, in Glycolipids: New Comprehensive Biochemistry (Neuberger et al., ed., Elsevier, 1985), pp. 199–260.

The monosialoganglioside GM2 has the structure:

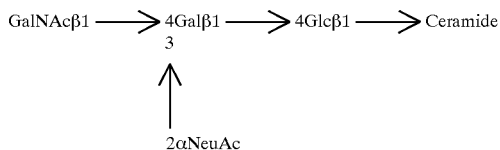

while GM1 has structure

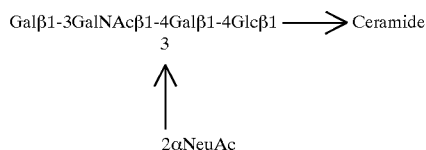

As noted, supra, the gangliosides are prevalent cell surface markers on transformed cells, such as melanoma. This has made them attractive targets for cancer research. Livingston, et al., Proc. Natl. Acad. Sci. USA 84: 2911–2915 (1987) incorporated by reference supra, describe results of a vaccine based trial, wherein subjects afflicted with melanoma received, as vaccines, either whole cells which present high levels of GM2, pure GM2 or pure GM2 plus bacterial adjuvant. Attention is also drawn to Livingston, et al., J. Clin. Oncol. 12(5): 1036–1044 (1994), and Irie, et al., U.S. Pat. No. 4,557,931, both of which are incorporated by reference, and deal with the use of GM2 as a vaccine.

There has also been interest in the manufacture and use of antibodies, such as monoclonal antibodies, which bind to gangliosides. Such antibodies share the common characteristics of all antibodies, including antigenic specificity, and are of interest both diagnostically and therapeutically. See, e.g., Kjeldsen, et al., U.S. Pat. No. 5,229,289; Nudelmann, et al., U.S. Pat. No. 5,240,833; Hakomori, et al U.S. Pat. No. 5,308,614, and Hakomori, et al., U.S. Pat. No. 5,389,530. All of these patents are incorporated by reference, and all deal in large part with the generation of ganglioside specific antibodies.

There are difficulties unique to the immunology of gangliosides, which are touched upon briefly here. First, while these molecules are prevalent on transformed cells, they are also common on certain normal cells, such as neural cells. There is a risk, in administering gangliosides to a subject, that the resulting antibody response will damage normal cells. Indeed, certain autoimmune pathologies, such as Guillain-Barre' Syndrome, are characterized by autoimmune antibodies reactive with GM1 or GQ1b. See, e.g., Yuki, et al., J. Exp. Med. 178: 1771–1775 (1993); Aspinall, et al., Infect & Immun. 62(5): 2122–2125 (1994).

There is an additional practical problem in that gangliosides are extremely difficult to secure in amounts sufficient for immunization protocols. No practical synthetic method is presently available. As a result, gangliosides are secured via purification from tissue, such as bovine cranial tissues. Even under optimum conditions, the yields of pure gangliosides are vanishingly small. Further, purification from mammalian tissue carries with it the risk of transmitting contaminants such as viruses, prion particles, and so forth. Alternate methodologies for securing ganglioside specific antibodies are thus highly desirable.

Lipopolysaccharide, or "LPS" molecules are found on the surface of Gram negative bacteria. Many of these molecules are quite toxic, leading to toxic shock syndrome, endotoxemia, and other conditions. There is a great deal of diversity in the LPS molecules of different bacteria. Indeed, even within the confines of a particular type of bacteria, the LPS molecule may differ, between various serotypes/serovars.

The LPS molecules of Campylobacter jejuni ("C. jejuni") have been studied in some detail. Representative, but by no means exhaustive, of the studies on these LPS molecules, are Aspinall, et al., Eur. J. Biochem. 213: 1017–1027 (1993); Aspinall, et al., Biochem. 33: 241–249 (1994); Yuki, et al., Infect. & Immun. 62(5): 2101–2103 (1994); Aspinall, et al., Infect. & Immun. 62(5): 2122–2125 (1994). All of these references are incorporated by reference. The Aspinall 1993 paper is of particular interest in that it presents LPS structures for C. jejuni serovars 0:1, 0:4, 0:23, and 0:36. Aspinall et al., state that OS:1, OS:23 and OS:36 are mutally indistinguishable, and have chain termini identical to those of GM2, while the OS:4 chain terminus is identical to GD1a. Some of these papers discuss certain similarities between portions of the 0:19 LPS molecule and GM1, an idea also discussed by Wirguin, et al., Ann. Neurol. 35(6): 698–703 (1994), incorporated by reference, as well as by Aspinall, et al., Infect. & Immun. 52(5): 2122–2125 (1994); Yuki, et al., Infect. & Immun. 62(5): 2102–2103 (1994); Yuki, et al., J. Exp. Med. 178: 1771–1775 (1993).

C. jejuni bacteria are themselves implicated in gastrointestinal disorders, and there has been some interest and activity in developing diagnostic tests for determining the presence of C. jejuni in samples. See PCT Application WO86/01808 to Wright et al., U.S. Pat. No. 5,200,344 to Blaser, et al., U.S. Pat. No. 5,169,757, to Yamazaki, et al., and Japanese Patent Application 63-273497 on this point. One notes that in all of these references, the manner in which the antibodies are generated involves the use of whole cells.

Blaser, et al., speak of an antigen unique to *C. jejnuni*, but it is a protein, not a glycolipid.

There has been no linking of *C. jejuni* LPS antigens are a source for producing antibodies against GM2. Further, there has been no suggestion that the antibodies produced in this way may be used in diagnostic and therapeutic approaches to pathological conditions, such as cancer.

These are all features of the invention described herein, in detail, in the disclosure which follows.

BRIEF DESCRIPTION OF THE FIGURES

FIG. 2A shows results obtained by testing pre-immune serum. The pre-immune serum was from a rabbit prior to immunization, tested with LPS 0:1, diluted 1:100 in PBS. The TLC was developed in two solvents (i.e., $CH_3Cl$ and acetone, at 1:1 ratio is the first solvent, the second solvent is $CHCl_3$, methanol, and 0.2% $CaCl_2$, at 55:45:10 ratio) prior to overlaying with serum. Moving across the lanes, lane 1 shows a test with mixed bovine brain gangliosides (10 ul) lane 2 tested bovine brain ganglioside GM2 (1 ug), lanes 3–5 tested, respectively, human melanoma (5 ul), human neuroblastoma (4 ul), and human renal carcinoma (5 ul) cell lines, while lane 6 tested fresh human melanoma (3 ul).

In FIG. 2B, immune serum from the same subject animal was tested. The serum was taken from the fifth bleed, and diluted 1:500 in PBS, as were the materials tested. Note that the upper bands, in lanes 5 and 6, were also found in these bands when pre-immune serum was tested, and thus are not a result of the immunization. In contrast, the lower bands in lanes 5 and 6 are the result of the immunization, while the upper bands are not.

In FIG. 3A, renal cell carcinoma cell line SK-RC-9, which is known to present GM2 on its surface was tested, while in FIG. 3B, colon carcinoma cell line SW 1222, which does not present GM2, was tested. In both figures, the open circles present data points where effector cells, target cells, and immune serum were combined. Filled in circles present data points from tests involving effector cells, target cells, and pre-immune serum, while filled in squares represent the combination of target cells and immune serum without effector cells.

DETAILED DESCRIPTION OF PREFERRED EMBODIMENTS

EXAMPLE 1

Figure 1:
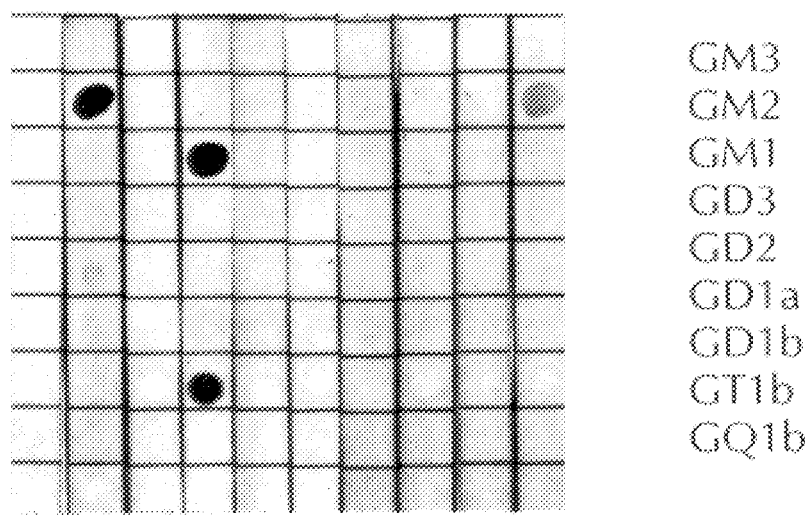
FIG. 1 is a dot blot showing results obtained, testing various ganglioside species, with antiserum obtained following immunization of rabbits with LPS prepared from various *Campylobacter jejuni* serovars. Lanes 1 and 2 used antiserum following immunization with 0:1, lanes 3 and 4 used 0:19, lanes 5 and 6 used 0:23, lanes 7 and 8 used 0:36, and lanes 9 and 10 used bovine brain ganglioside GM2. Odd numbered lanes are tests with pre-immune serum, and even numbers are immune serum.

All bacteria used were obtained from the American Type Culture Collection. Samples of *Campylobacter jejuni* ("*C. jejuni*" hereafter) of serotype 0:1, 0:19, 0:23, and 0:36 were used. For each sample, the lipopolysaccharide antigens ("LPS" antigens hereafter) were extracted from heat inactivated bacteria, using the hot phenol-water methodology of Westphal, et all, Z. Naturforschlag. 7b: 148–155 (1952), incorporated by reference herein with minor modifications. Specifically, RNA was removed by digestion with commercially available bovine pancreas RNA, followed by size exclusion chromatography on Sephadex G-25 in accordance with Goldman, Meth. Enzymol. 138: 267–275 (1987). The extracted LPS was lyophilized, and stored at −20° C. until ready for use.

EXAMPLE 2

The LPS preparations were then used to prepare immunogenic compositions. In each case, the LPS antigen was mixed with adjuvant. For each composition, two rabbits were used as subject animals (female New Zealand white rabbits, 2–2.5 kg in weight). On day 0, the animals were injected, intradermally, with 500 ug of LPS in Complete Freunds Adjuvant. Fourteen days later, the animals received a second injection of 500 ug of LPS, this time in Incomplete Freund's Adjuvant. This was followed up with injections at day 28 and day 42, in each case with 250 ug of LPS in Incomplete Freund's adjuvant. Two animals were injected with pure bovine brain GM2, (200 ug, 200 ug, 100 ug, 100 ug, at the same time points in the experiment). All animals were bled at days 0, 14, 28, 42 and 64, to determine antibody titer and to conduct additional analyses. Some rabbits were also given booster injections of 250 ug LPS in IFA, 13 and 17 weeks after the fourth injection, and were bled two weeks after the last booster injection.

EXAMPLE 3

With reference to the immunization protocol described, supra, following each bleed, sera from the immunized rabbits were analyzed, via a standard ELISA, to determine (i) if antibodies against GM2 were present, and (ii), if so, were these of class IgG, or IgM. This was done using commercially available antirabbit IgM or IgG antibodies. Immunization with *C. jejuni* serovar 0:1 yielded IgG antibodies, and high titer serum (1:3200, and ≧60,000 after booster injections), as well as low titer IgM antibodies (1:100), both of which recognized GM2. The immunization with *C. jejuni* 0:36 yielded moderate titer IgM antibodies (1:800), and low titer IgG antibodies (1:100). These also recognized GM2. The immunization with 0:19 yielded high titer IgG antibodies (peak: 1:12800), and moderate to high titer IgM antibodies (peak: 1:1200); however, these antibodies recognized ganglioside GM1. The test with pure, bovine brain GM2 yielded low titer IgM (1:200), and IgG (1:200).

EXAMPLE 4

The sera obtained as described, supra, was analyzed thoroughly for specificity in dot blot assays. The sera were stained for IgM and IgG antibodies to GM2, and also to a panel of other gangliosides derived from bovine brain material, including GM3, GM1, GD3, GD2, GD1a, GD1b, GT1b, and GQ1b, immobilized on nitrocellulose paper. The results follow, in Table 1. The dot blot assay was a standard one, using serum dilutions of 1:100 and commercially available anti-rabbit IgG and IgM antibodies. In table 2, which follows, a grade of "3+" means that there was strong staining, "2+" a medium-strong stain, "1+", a weak stain, and "+/", a trace of staining. FIG. 1, which follows, presents the dot blots.

TABLE 1

IgG reactivity of Immune Sera with Gangliosides and LPS as determined by Dot Blot Immune Stains

| Animal | Vaccine | Serum* | GM3 | GM2 | GM1 | GO3 | GO2 | GO1a | GO1b | GT1b |
|---|---|---|---|---|---|---|---|---|---|---|
| 1 | LPS 0:1 | pre-vacc. | — | — | — | — | — | — | — | — |
| 1 | " | 4. vacc. | — | 3+ | — | — | — | — | — | — |
| 2 | " | pre-vacc. | — | — | — | — | — | — | — | — |
| 2 | " | 4. vacc. | — | 2+ | — | — | — | — | — | — |
| 3 | LPS0:19 | pre-vacc. | — | — | — | — | — | — | — | — |
| 3 | " | 4. vacc. | — | — | 3+ | — | — | 1+ | 2+ | — |
| 4 | " | pre-vacc. | — | — | — | — | — | — | — | — |
| 4 | " | 4. vacc. | — | — | 3+ | — | — | — | 3+ | — |
| 5 | LPS0:23 | pre-vacc. | — | — | — | — | — | — | — | — |
| 5 | " | 4. vacc. | — | — | — | — | — | — | — | — |
| 6 | " | pre-vacc. | — | — | — | — | — | — | — | — |
| 6 | " | 4. vacc. | — | — | — | — | — | — | — | — |
| 7 | LPS0:36 | pre-vacc. | — | — | — | — | — | — | — | — |
| 7 | " | 4. vacc. | — | — | — | — | — | — | — | — |
| 8 | " | pre-vacc. | — | — | — | — | — | — | — | — |
| 8 | " | 4. vacc. | — | — | — | — | — | — | — | — |
| 9 | GM2 | pre-vacc. | — | — | — | — | — | — | — | — |
| 9 | " | 4. vacc. | — | 1+ | — | — | — | — | — | — |
| 10 | " | pre-vacc. | — | — | — | — | — | — | — | — |
| 10 | " | 4. vacc. | — | 2+ | — | — | — | — | — | — |

*serum dilution 1:100

As will be seen in Table 1, there was strong serum IgG reactivity with GM2 from animals immunized with C. jejuni serovar 0:1LPS, while the other serum samples tested negative. The sera from C. jejuni serovar 0:19 immunized animals showed strong reactivity with GM1, and moderately strong activity with GD1b. Weak reactivity with GD1a was also seen.

EXAMPLE 5

Figure 2A:
FIGS. 2A and 2B present data obtained in immune thin layer chromatography tests.
Figure 2B:
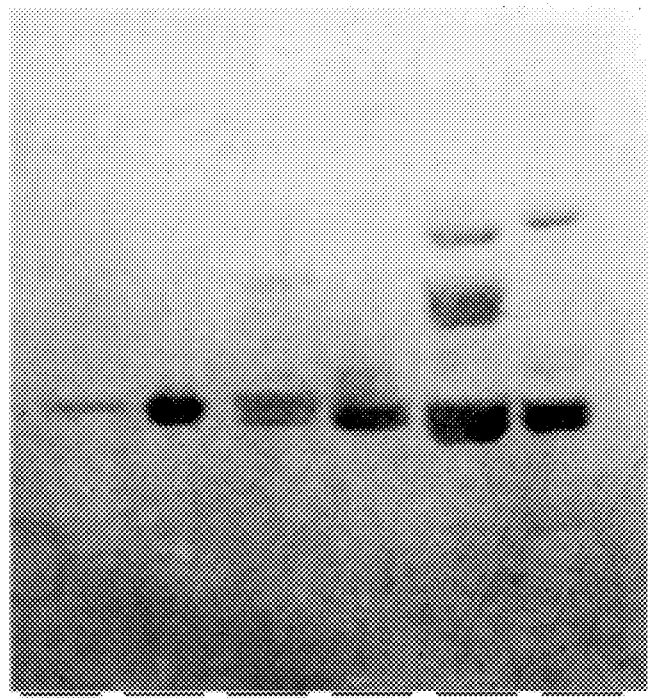

In further experiments, the sera were tested, in immune thin layer chromatography, for reactivity with purified bovine brain GM2, and with GM2 extracted from fresh human melanoma, a human renal cell carcinoma cell line, a human melanoma cell line, and from a human neuroblastoma cell line. The immune thin layer chromatography tests were carried out using standard methodologies. The IgG antibodies obtained from sera of animals immunized with C. jejuni serovar 0:1 reacted strongly with all sources of GM2. FIGS. 2A and 2B show these results. The IgG antibodies obtained from sera obtained from C. jejuni serovar 0:19 immunized animals reacted strongly with purified bovine brain GM1.

EXAMPLE 6

The ability of the GM2 specific sera to bind to cell surfaces was tested in a standard mixed hemadsorption assay. In this assay, human renal carcinoma cell line SK-RC-9, which expresses high levels of cell surface GM2 on its surface, was combined with the sera obtained from animals immunized with C. jejuni serovar 0:1 LPS. the antibodies in the sera were surface reactive (peak titer 1:600). See following Table 2.

TABLE 2

Cell surface reactivity of immune sera with SK-RC-9 as determined by mixed hemesorption assays

| | | | Titer* | |
|---|---|---|---|---|
| Animal | Vaccine | Serum | IgM | IgG |
| 1 | LPS C. jejuni 0:1 | pre-vacc. | – | +/– |
| 1 | " | 2. wks post 1. vacc. | +/– | 1:100 |
| 1 | " | 2. wks post 2. vacc. | – | 1:300 |
| 1 | " | 2. wks post 4. vacc. | – | 1:600 |
| 2 | " | pre-vacc. | – | +/– |
| 2 | " | 2. wks post 1. vacc. | 1:100 | +/– |
| 2 | " | 2. wks post 2. vacc. | – | +/– |
| 2 | " | 2. wks post 4. vacc. | +/– | 1:150 |
| 2 | " | 2. wks post 6. vacc. | 1:2000 | 1:1600 |
| 9 | GM2 ganglioside | pre-vacc. | +/– | – |
| 9 | " | 2. wks post 1. vacc. | +/– | – |
| 9 | " | 2. wks post 2. vacc. | +/– | +/– |
| 9 | " | 2. wks post 4. vacc. | 1:300 | 1:400 |
| 10 | " | pre-vacc. | – | +/– |
| 10 | " | 2. wks post 1. vacc. | +/– | +/– |
| 10 | " | 2. wks post 2. vacc. | 1:100 | +/– |
| 10 | " | 2. wks post 4. vacc. | +/– | +/– |

*Starting dilution of serum: 1:100

EXAMPLE 7

Further experiments were carried out to test for the presence of antibodies which mediate antibody-dependent cellular cytotoxicity ("ADCC"). These experiments involved the well known $^{51}$Cr release assay.

Figure 3A:
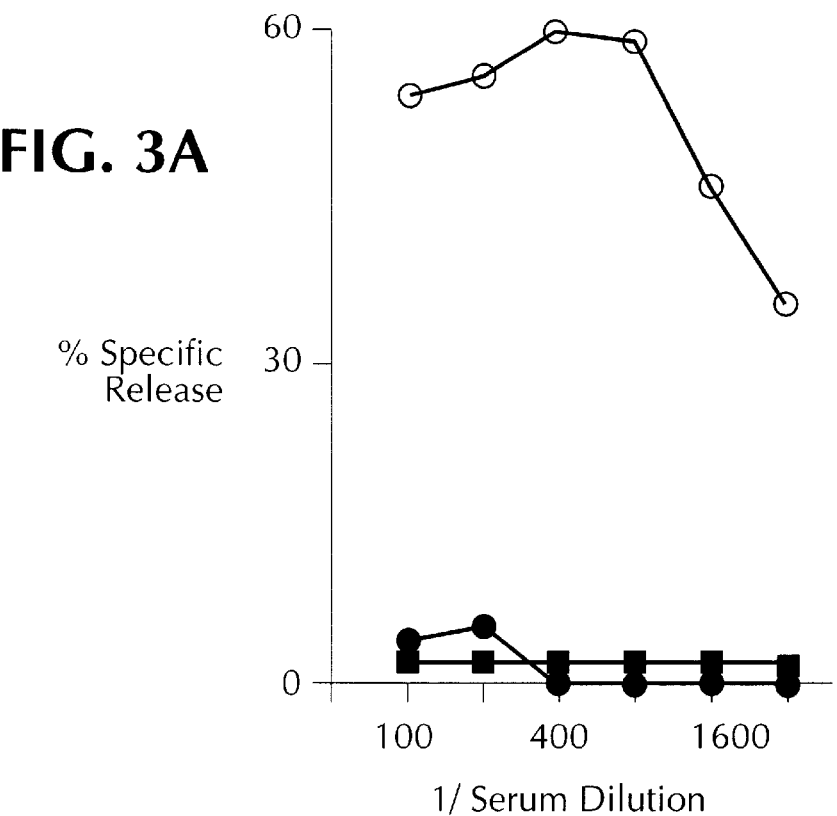
FIGS. 3A and 3B depict the results obtained in antibody dependent cellular cytotoxicity tests. The serum used was obtained following immunization with LPS serotype 0:1.
Figure 3B:
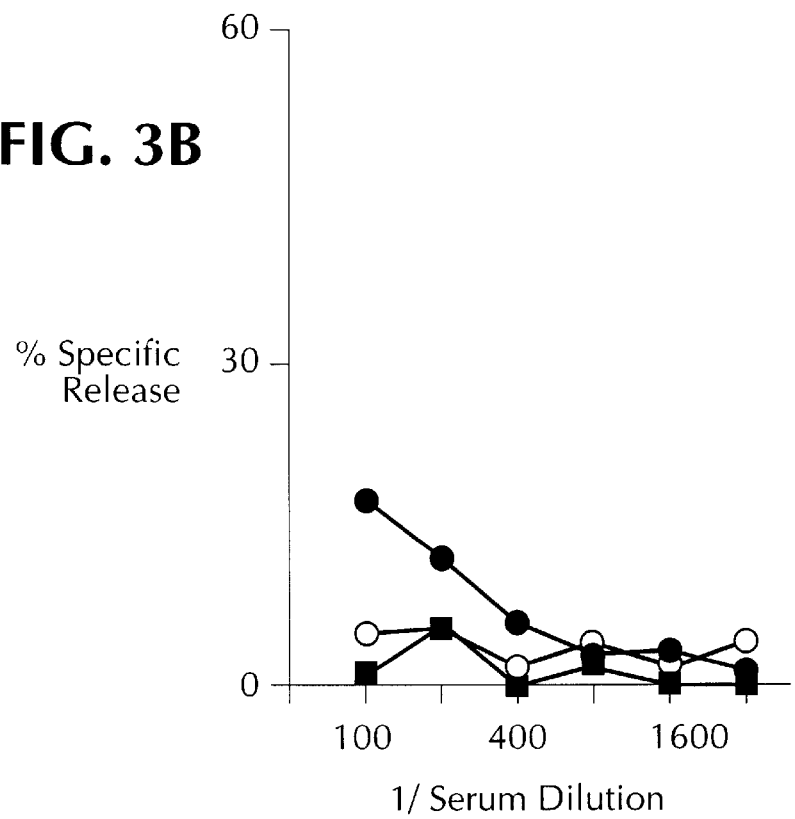

In these experiments, serum obtained from rabbits which had received six vaccinations with LPS isolated from C. jejuni serotype 0:1 was combined with various tumor cell lines. The antibodies were cytotoxic to GM2 expressing tumor cell lines, including renal cell carcinoma cell line SK-RC-9 (up to 60% specific killing, at serum dilutions of 1:800), and neuroblastoma cell line 1MR-32 (up to 80% specific killing, at serum dilutions of 1:800); SK-Mel-31 (a melanoma cell line; up to 35% specific lysis), and renal cell carcinoma SK-RC-49 (35% specific lysis, at 1:400 serum dilutions. There was no specific lysis found for those cell lines which did not present GM2 on their surfaces. Normal rabbit serum did not mediate cell lysis either. This will be seen in FIG. 3.

The foregoing examples set forth a process for making antibodies specific for a ganglioside, i.e., GM2 or GM1. The it methodology is surprising in that the immunogen is not a ganglioside. As is seen, supra, immunization with a molecule of structure GalNAcβ1-4Gal(II³NeuAc)-Hex, generated anti-GM2 specific antibodies, while immunization with an immunogen of structure Galβ1-3GalNAcβ1-4Gal (II³NeuAc) generated anti-GM1 specific antibodies. These molecules are not gangliosides.

The immunogen used is preferably a lipopolysaccharide molecule, most preferably an LPS molecule secured from *C. jejuni*. As will be seen from the discussion, supra, different serovars of *C. jejuni* have different LPS molecules on their surface. It is well within the skill of the artisan to carry out analyses to determine if a molecule, such as an LPS molecule has the desired structure as per Aspinall, et al., 1993, supra, e.g. Thus, the invention is not limited to the use of the specific serovars discussed herein.

It is preferred that the immunogens be administered together with an adjuvant, such as the described Complete and Incomplete Freund's Adjuvant. Other adjuvants, including, e.g., *Bortadella pertussis*, aluminum hydroxide, QS-21, BCG, *Salmonella Minnesota* R595, adjuvant, MPL and other adjuvants well known to the art may be used. Similarly, the immunogen may be used "as is", such as described herein, or it may be coupled to materials which enhance its immunogenicity, such as Keyhole limpet hemocyanin, bovine serum albumin, etc.

The subject animal may be any of the standard mammalian hosts used in the art for generating antibodies, including mice, rats, and other rodents; sheep, goats, and other ruminants, and so forth.

The antibodies described herein are polyclonal in nature. It is assumed, however, that one of ordinary skill is fully able to work with materials which generate the disclosed polyclonal antibodies so as to develop hybridomas and monoclonal antibodies. Such methodologies, including the well known Köhler-Milstein method and other ways to "immortalize" antibody producing B cells, need not be set forth here.

While one does not use humans as test animals, the ability to generate antibodies against these LPS structures does provide the artisan with an appropriate way to vaccinate individuals to achieve active, rather than passive immunization. The art is fully familiar with methodologies which eliminate the toxic effect of LPS molecules without significantly modifying their immunogenicity. It has been shown, that mammalian immune systems can, and do react to these LPS molecules to produce antibodies against GM2. It has also been shown that various types of cancer, such as renal carcinoma, neuroblastoma carcinoma, sarcoma, glioma, seminoma and melanoma, are characterized in part by expression of GM2 molecules on their surface. Vaccination with non-toxic forms of LPS, including those used in the examples described herein, should lead to immunological clearance of GM2 presenting cancer cells. Hence one aspect of the invention relates to a method for treating a subject with a pathological condition, such as a cancer, where abnormal cells present GM2 on their surfaces, by administering an effective amount of a non-toxic LPS molecule to the subject, so as to provoke production of anti-GM2 antibodies in said subject.

As is shown in the examples, supra, antibodies produced in the manner described are useful diagnostically, as in the determination of whether or not cells are present in a sample which present gangliosides GM1 or GM2 on their surface. Thus, one is able to screen a sample for irregularities, such as the onset of tumorigenicity, where tumor cells present GM1 or GM2 on their surface, while non-transformed cells do not. Melanoma and renal carcinoma are examples of such transformed cells. Similarly, samples can be analyzed generally, using the antibodies described herein. For example, a bovine brain fraction can be assayed to determine whether or not desired gangliosides GM1 and/or GM2 are present, and if so, whether or not they are present in an amount to warrant further analysis and purification.

The work described supra as it relates to vaccines also provides support for another aspect of the invention, which is a method for treating a pathological condition, such as melanoma, neuroblastoma, sarcoma, glioma, seminoma, and other types of cancer wherein the pathology is characterized by appearance of GM2 or GM1 on abnormal cells. One may administer a therapeutically useful dose of the antibodies of the invention sufficient to provide a therapeutically positive effect to the subject so treated.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A process for making an antibody which binds to monosialoganglioside GM1, comprising:

(i) immunizing a subject animal with an antigen comprising the structure:

Galβ1→3Gal NAcβ1→4Gal (II³NeuAc)

in an amount sufficient to provoke production of antibody by said animal with the proviso that the antigen is not GM1, and (ii) isolating the antibodies produced by said animal.

2. The process of claim 1, wherein said antigen is a lipopolysaccharide.

3. The process of claim 2, wherein said lipopolysaccharide is purified lipopolysaccharide from a gram negative bacteria.

4. The method of claim 3, wherein said gram negative bacteria are *Campylobacter jejuni*.

5. The process of claim 2, wherein said *Campylobacter jejuni* are of serotype 0:19.

6. The process of claim 2, wherein said lipopolysaccharide is combined with an adjuvant.

7. The process of claim 6, wherein said adjuvant is Complete Freund's Adjuvant or Incomplete Freund's Adjuvant.

8. A method for determining presence of monosialoganglioside GM1 in a sample, comprising contacting said sample with the antibody produced in accordance with the claim 1, and determining binding of said antibody as a determination of GM1 in said sample.

9. The method of claim 8, wherein said sample contains transformed cells.

10. The method of claim 9, wherein said transformed cells are melanoma cells, neuroblastoma cells, sarcoma cells, glioma cells, or seminoma cells.

11. A process for making an antibody which binds to monosialoganglioside GM1, comprising:

(i) immunizing a subject animal with a purified lipopolysaccharide obtained from a gram negative bacteria which comprises the structure:

Gal β1-3GalNAcβ1-4Galβ (II3neuAc) in an amount sufficient to provoke production of antibody by said animal, and (ii) isolating the antibodies produced by said animal.

* * * * *